US006339216B1

United States Patent
Wake

(10) Patent No.: US 6,339,216 B1
(45) Date of Patent: *Jan. 15, 2002

(54) TIME-RESOLVED BREAST IMAGING DEVICE

(75) Inventor: Robert H. Wake, Copper City, FL (US)

(73) Assignee: Imaging Diagnostic Systems, Inc., Plantation, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/199,440

(22) Filed: Nov. 25, 1998

Related U.S. Application Data

(60) Provisional application No. 60/066,479, filed on Nov. 26, 1997.

(51) Int. Cl.⁷ ................................................ H01J 40/14
(52) U.S. Cl. ................................ 250/214 A; 250/214 AG; 250/363.02; 600/407
(58) Field of Search ...................... 250/214 R, 214 A, 250/330, 363.04, 363.05, 363.08, 363.02, 363.03, 370.09, 208.1, 214 AG; 600/407, 473, 425, 476, 475; 330/278–281; 382/131

(56) References Cited

U.S. PATENT DOCUMENTS

| | | |
|---|---|---|
| 3,863,154 A | 1/1975 | Marwell et al. ............... 368/114 |
| 4,499,430 A | 2/1985 | Fujii .............................. 330/279 |
| 4,554,460 A | 11/1985 | Klein ......................... 250/208.2 |
| 5,408,093 A | 4/1995 | Ito et al. .................. 250/227.26 |
| 5,471,049 A | 11/1995 | Cain ........................... 250/208.2 |
| 5,477,051 A | 12/1995 | Tsuchiya .................... 250/341.1 |
| 5,572,118 A | 11/1996 | Lewis ........................ 324/123 R |
| 5,692,511 A | * 12/1997 | Grable ........................... 600/425 |
| 5,694,938 A | 12/1997 | Feng et al. ................... 600/425 |
| 5,708,414 A | 1/1998 | Peltier et al. ................. 340/506 |
| 5,717,608 A | 2/1998 | Jensen ........................... 702/130 |
| 5,719,398 A | 2/1998 | Colak ......................... 250/341.1 |
| 5,813,987 A | 9/1998 | Modell et al. ................ 600/473 |
| 5,815,410 A | 9/1998 | Heinke et al. ................ 702/135 |
| 5,821,541 A | * 10/1998 | Turner ..................... 250/370.09 |
| 5,851,181 A | 12/1998 | Talmor .......................... 600/407 |
| 5,880,827 A | 3/1999 | Heinke ......................... 356/224 |

* cited by examiner

*Primary Examiner*—Que T. Le
*Assistant Examiner*—Thanh X. Luu
(74) *Attorney, Agent, or Firm*—Shlesinger, Arkwright & Garvey LLP

(57) ABSTRACT

A photodetection circuit for use in a laser imaging apparatus comprises a photodetector adapted to respond to a laser pulse exiting from a breast being scanned; a multi-gain preamplifier circuit connected to the output of the photodetector; a switch connected to the output of the multi-gain preamplifier for sampling the output of the photodetector; an RC circuit for spreading the sampled signal; an amplifier connected to the output of the RC circuit; and an integrator for integrating each sample of the output. A time-gating circuit is operably connected to the switch to open and close the switch at regular intervals of time during the occurrence of the output. A laser pulse synchronization circuit is operably connected to the time-gating circuit to provide a signal to the time-gating circuit as to when the laser pulse is expected to arrive at the photodetector.

18 Claims, 16 Drawing Sheets

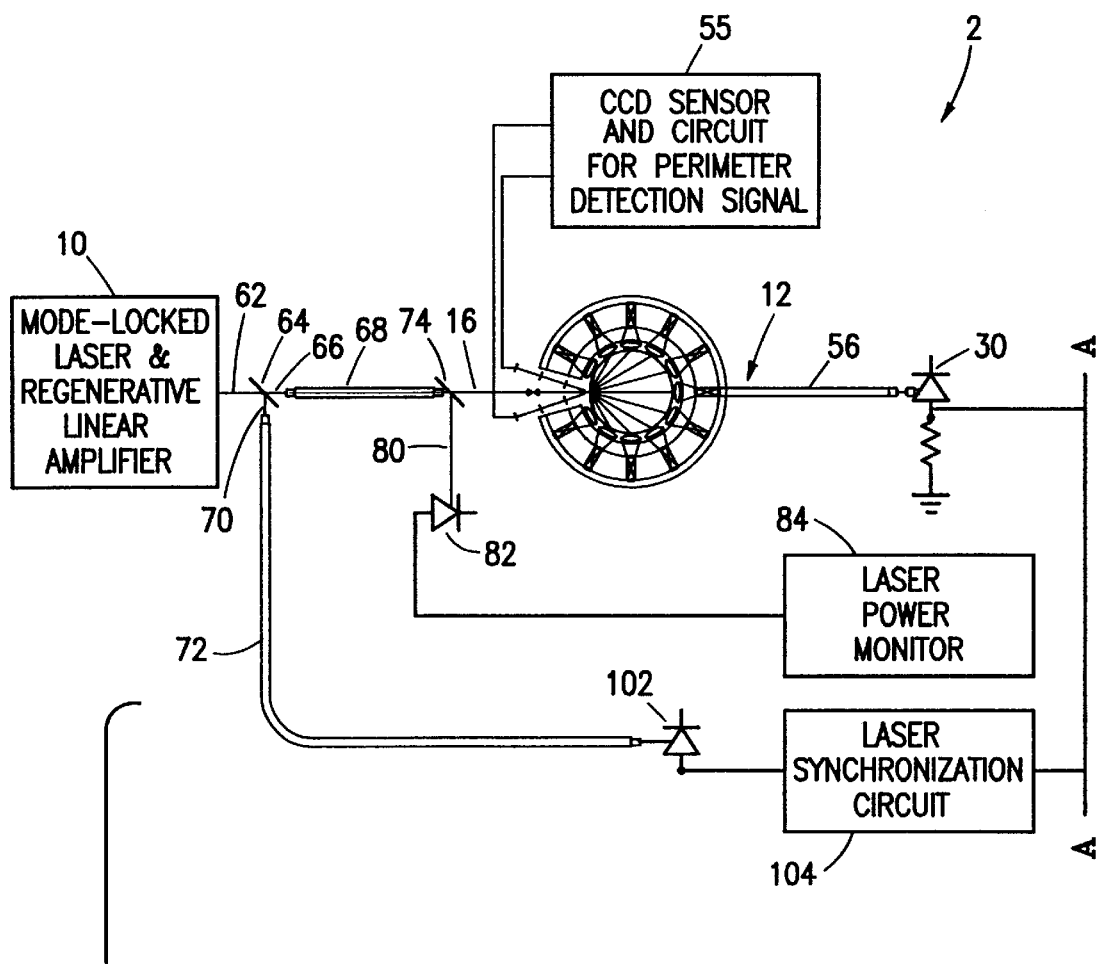
FIG. 8
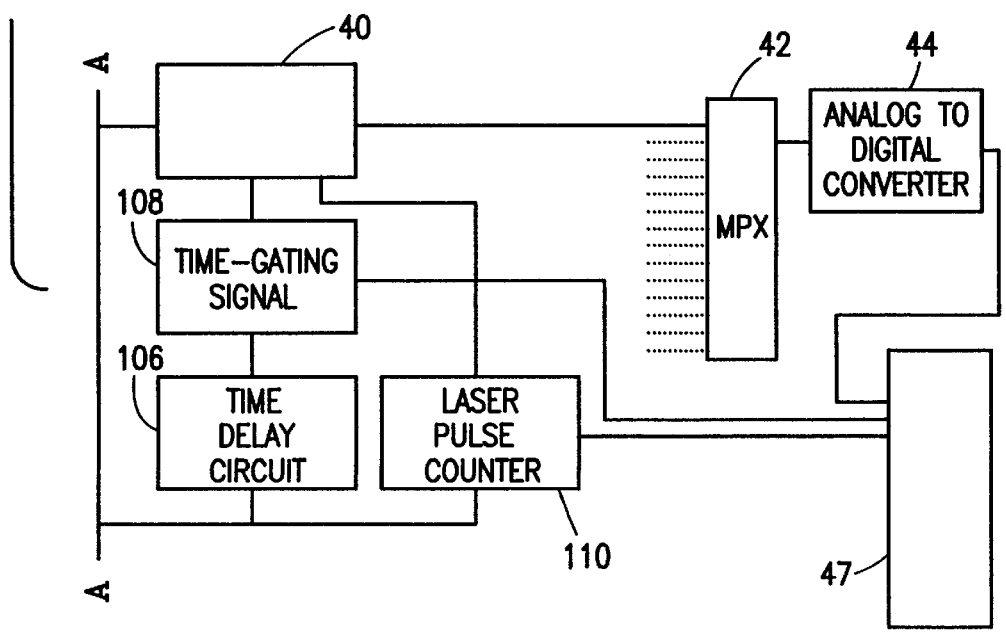

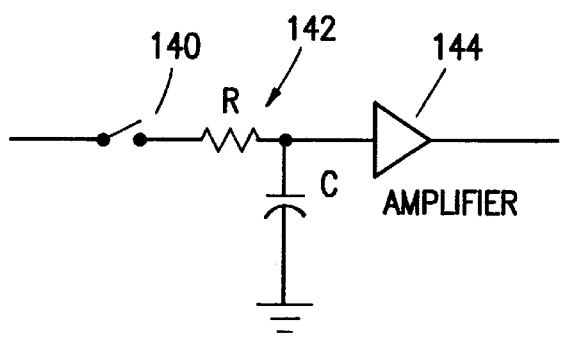
FIG. 16A
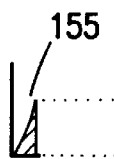 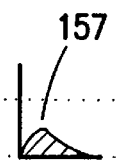 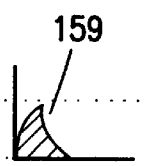
FIG. 16B   FIG. 16C   FIG. 16D

TIME-RESOLVED BREAST IMAGING DEVICE

This application claims benefit to Provisional application No. 60/066,479 filed Nov. 26, 1997.

FIELD OF THE INVENTION

The present invention relates generally to a diagnostic medical imaging apparatus and more particularly to a mammography machine that employs a near-infrared laser as a radiation source.

BACKGROUND OF THE INVENTION

Cancer of the breast is a major cause of death among the American female population. Effective treatment of this disease is most readily accomplished following early detection of malignant tumors. Major efforts are presently underway to provide mass screening of the population for symptoms of breast tumors. Such screening efforts will require sophisticated, automated equipment to reliably accomplish the detection process.

The x-ray absorption density resolution of present photographic x-ray methods is insufficient to provide reliably early detection of malignant tumors. Research has indicated that the probability of metastasis increases sharply for breast tumors over 1 cm in size. Tumors of this size rarely produce sufficient contrast in mammogram to be detectable. To produce detectable contrast in photographic mammogram, 2–3 cm dimensions are required. Calcium deposits used for inferential detection of tumors in conventional mammography also appear to be associated with tumors of large size. For these reasons, photographic mammography has been relatively ineffective in the detection of this condition.

Most mammographic apparatus in use today in clinics and hospitals require breast compression techniques which are uncomfortable at best and in many cases painful to the patient. In addition, x-rays constitute ionizing radiation which injects a further risk factor into the use of mammographic techniques as most universally employed.

Ultrasound has also been suggested, as in U.S. Pat. No. 4,075,883, which requires that the breast be immersed in a fluid-filled scanning chamber. U.S. Pat. No. 3,973,126 also requires that the breast be immersed in a fluid-filled chamber for an x-ray scanning technique.

U.S. Pat. No. 5,692,511 discloses a laser imaging apparatus.

In recent times, the use of light and more specifically laser light to non-invasively peer inside the body to reveal the interior structure has been investigated. This technique is called optical imaging. Optical imaging and spectroscopy are key components of optical tomography. Rapid progress over the past decade have brought optical tomography to the brink of clinical usefulness. Optical wavelength photons do not penetrate in vivo tissue in a straight line as do x-ray photons. This phenomena causes the light photons to scatter inside the tissue before the photons emerge out of the scanned sample.

Because x-ray photon propagation is essentially straight-line, relatively straight forward techniques based on the Radon transform have been devised to produce computed tomography images through use of computer algorithms. Multiple measurements are made through 360° around the scanned object. These measurements, known as projections, are used to backproject the data to create an image representative of the interior of the scanned object.

In optical tomography, mathematical formulas and projection techniques have been devised to perform a reconstruction function somewhat similar to x-ray tomography. However, because light photon propagation is not straight-line, techniques to produce cross-section images are mathematically intensive and invariably require establishing the boundary of the scanned object. Boundary determination is important because it serves as the basis for reconstruction techniques to produce interior structure details. Algorithms to date do not use any form of direct measurement technique to establish the boundary of the scanned object.

Photon propagation through breast tissue does not follow a straight line and can best described as "drunkard's walk". The mean free path of a photon within the breast is on the order of 1 mm, and after this short distance the photon is deflected at a different direction. In general, the photons are said to be forward scattered with the mean of the cosine of the scattering angle on the order of 0.9. The index of refraction of breast tissue is approximately 1.5 and thus the speed of photon travel within the breast is on the order of $2 \times 10_8$ meters per second.

In accordance with the present invention, knowledge of the propagation of light through the breast tissue, determination of the perimeter of the breast at the selected scanning location, and the known configuration of the scanner allow a method of selecting those photons that travel the shortest path through the breast to be used to produce a computed tomography of the interior of the breast.

OBJECTS AND SUMMARY OF THE INVENTION

It is an object of the present invention to provide a detector array that can detect the significantly different light levels emerging from a scanned object.

It is another object of the present invention to provide a processing circuit for a detector that can accommodate the dynamic range of the detector.

It is still another object of the present invention to provide a detector with multiple gain amplifier to accommodate the dynamic range of the detector signal, which could range in relative amplitude from approximately $10^{-11}$ to 1.

It is another object of the present invention to provide a processing circuit that can detect the earliest arriving photons exiting from the breast being scanned.

It is another object of the present invention to acquire data to allow reconstruction of contiguous cross-section images of the interior of a breast using short pulses of near infrared light.

It is an object of the present invention to provide a direct determination of the boundary of the scanned object, thus eliminating a significant portion of the time required to reconstruct an interior image of the scanned object.

It is another object of the present invention to provide one or more sensors placed on the same side of the scanned object as the impinging radiation to detect the location of the point of contact of the impinging beam on the scanned object and using this information to determine the boundary of the object.

It is another object of the present invention to provide a means for directing a laser beam into the breast by use of a fiber optic cable and to couple light collected by a collimator to a photodetector.

It is another object of the present invention to provide a means by synchronizing the data acquisition circuits to the arrival of photons delivered through fiber optic cable and optics.

It is another objective of the present invention to provide processing circuit to allow acquiring data to determine the TPSF for each scan location, and use the TPSF to estimate the transport scattering coefficient, $\mu_s'$, and the absorption coefficient, $\mu_a$.

It is still another objective of the present invention to provide data for imaging reconstruction through use of all or time-gated portions of the TPSF data.

In summary, the present invention provides a detector array for a laser imaging apparatus, comprising a plurality of detectors disposed in an arc around an opening in which an object to be scanned is disposed; and a multi-gain amplifier circuit connected to each detector.

The present invention also provides a detector array for a laser imaging apparatus, comprising a plurality of detectors disposed in an arc around an opening in which an object to be scanned is disposed; and a multi-gain amplifier circuit means for processing the output of each detector to provide data for use in image reconstruction.

The present invention further provides a photodetection circuit for use in a laser imaging apparatus, comprising a photodetector adapted to respond to a laser pulse exiting from a breast being scanned; a multi-gain preamplifier circuit connected to the output of the photodetector; a switch connected to the output of the multi-gain preamplifier for sampling the output of the photodetector; an RC circuit for spreading the sampled signal; an amplifier connected to the output of the RC circuit; and an integrator for integrating each sample of the output. A time-gating circuit is operably connected to the switch to open and close the switch at regular intervals of time during the occurrence of the output. A laser pulse synchronization circuit is operably connected to the time-gating circuit to provide a signal to the time-gating circuit as to when the laser pulse is expected to arrive at the photodetector.

The present invention still provides a method for collecting data for use in image reconstruction of an object being scanned, comprising providing a plurality of detectors disposed in an arc around the object to be scanned; connecting a multi-gain amplifier circuit to each detector; impinging a laser beam at a point on the object; sampling the output curve of each detector in sufficient time intervals to recreate the curve; integrating each sample; repeating the sampling and integrating for a number of laser pulses; recording each output for each pulse for use in image reconstruction; orbiting the detectors and the laser beam to another point on a circle; and repeating the above until a complete circle has been traversed.

The present invention also provides an apparatus for determining the perimeter of an object being scanned, comprising a scanning chamber for receiving therein an object being scanned; a source of laser beam disposed within said scanning chamber for impinging on the object being scanned, said laser beam being adapted to orbit around the object; an array of sensors disposed within said chamber, each of said sensors being adapted to detect light reflecting from the surface of the object due to said laser beam exiting from the object; each of said sensors being disposed such that at least only one of said sensors generates a peak response to light emanating from a point on the surface at a predetermined distance from a reference point, such that at each angular position of said laser beam in the orbit, a specific point at a distance from the reference is determined, thereby to generate a set of points representing the perimeter of the surface after a complete orbit.

These and other objectives of the present invention will become apparent from the following detailed description.

BRIEF DESCRIPTIONS OF THE DRAWINGS

FIG. 8 is a schematic diagram of the scanning apparatus of FIG. 1.

FIGS. 16A, 16B, 16C and 16D are a schematic diagram of a RC circuit used in the present invention and the associated waveforms.

DETAILED DESCRIPTION OF THE INVENTION

Figure 1:
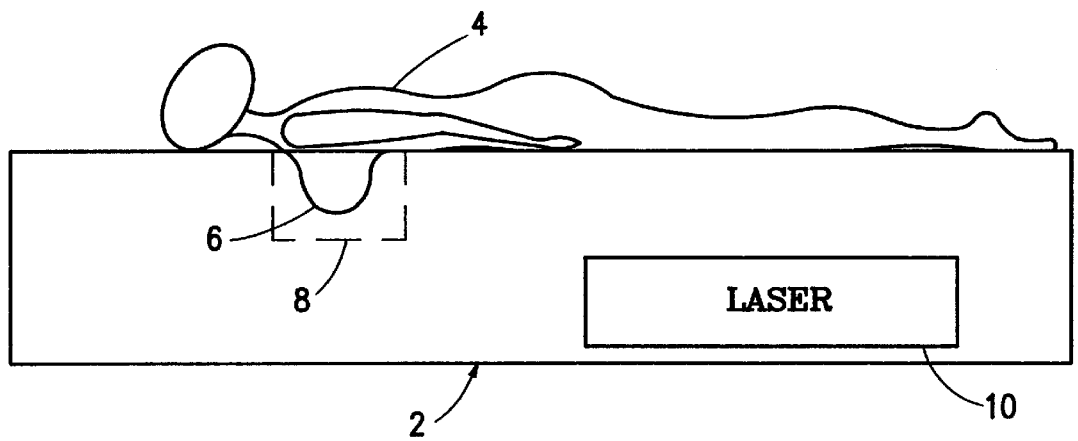
FIG. 1 is a schematic side elevational view of an optical imaging apparatus made in accordance with the present invention, showing a patient on a support platform with one of her breasts positioned within a scanning chamber configured to exclude ambient light.

A scanning apparatus 2, such as that described in U.S. Pat. No. 5,692,511, which is hereby incorporated by reference, is schematically disclosed in FIG. 1. A patient 4 is positioned prone on a top surface of the apparatus 2 with her breast 6 pendent within a scanning chamber 8 configured to exclude ambient light. A laser beam from a laser source 10 is operably associated with the scanning chamber 8 to illuminate the breast 6.

Figure 2:
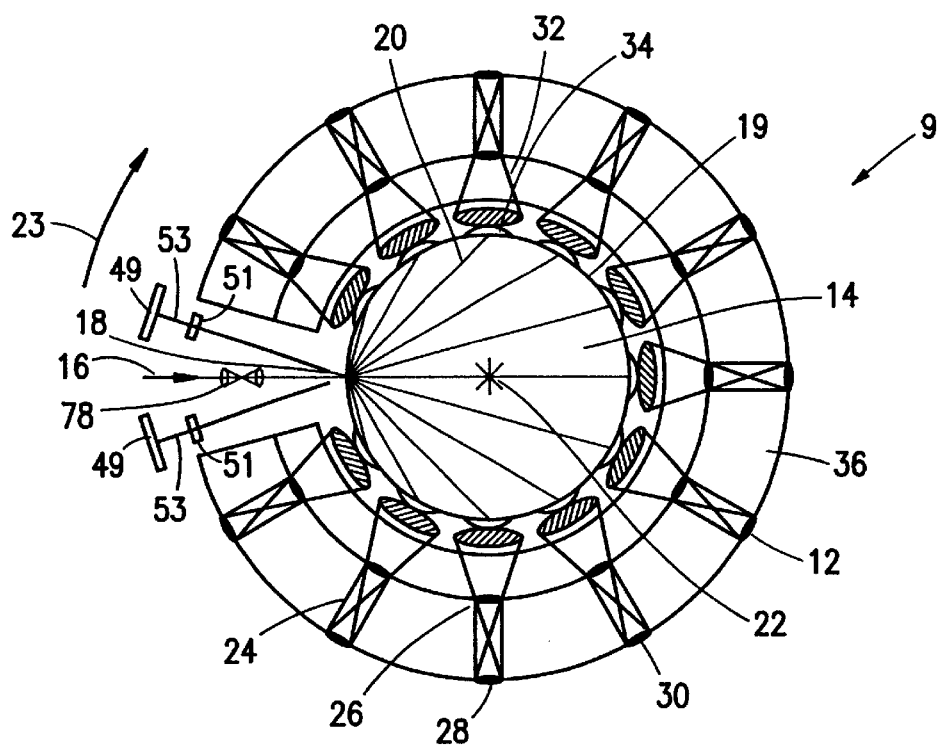
FIG. 2 is a schematic top view of a scanning chamber, showing the geometrical relationships between a laser beam, an array of photodetector assemblies and an arrangement for determining the perimeter of an object being scanned.

The scanning chamber 8 includes a scanner 9 and is shown schematically in plan view in FIG. 2. The scanning chamber includes a plurality of detector assemblies 12 disposed in an arc to define an opening in which an object 14 to be scanned, such as the breast, is positioned. A laser beam 16 impinges the object at point 18. Light exiting from the object 14, such as the rays 20, is picked up by the respective detector assemblies 12, that is then used to provide an image of the scanned object. The rays 20 are assumed to take the paths represented by chords originating from the point of entry 18 of the laser beam 16 and exiting at various points on the perimeter 19 of the scanned object.

The detector assemblies 12 are digitally orbited around the object 14 about an orbit center 22 at equal angular increments for a total angular displacement of 360° in a direction generally indicated at 23. The object 14 is illuminated with the laser beam 16 at each angular position in the orbit 23. The light emerging from the object depicted by the chords 20 on the perimeter of the scanned object, at one instant in time or in a period of time acquired simultaneously, is picked up by the respective detector assemblies 12. Each detector assembly has its longitudinal axis directed toward the orbit center 22. The detector assemblies 12 are secured to a support 36, which is orbited in orbit 23 around the object 14 being scanned.

After each complete orbit, the array of detector assemblies 12 and the laser beam 16 are moved vertically to a new position to scan a different slice plane of the object. This is repeated until all the slice planes of the object has been scanned.

Each detector assembly 12 includes an opaque housing 24 with an open front end 26 and a rear end 28 in which a detector 30 is disposed. Preferably, each detector 30 is disposed remotely from the housing 24 by means of a fiber optic cable that connects the respective detector to the respective housing (see FIG. 6), as will be discussed below. The inside surface of the housing 24 can be tubular, round, square or other cross-sectional shape. The housing 24 is designed to restrict the field of view of its respective detector 30, such that each detector is only looking at its own small area of the scanned object. The field of view of each detector assembly 12 is schematically indicated at 32. A patch or surface seen on the scanned object by the respective detector assembly is schematically indicated at 34.

The field of view 32 and the respective patch of surface 34 are configured such that adjacent patches of surface minimally overlap each other. In this way, each detector assembly is uniquely assigned to a patch of surface at each angular position of the orbit so that light coming from one patch of surface could only be detected by the respective detector whose field of view covers that particular patch of surface. Each detector 30 is active to detect any light emerging from its respective patch of surface, since the light beam 16 can course through the object in any paths, such as those depicted by the chords 20. Each housing is further described in copending application Ser. No. 08/963,760 filed Nov. 4, 1997, claiming priority based on provisional applications Ser. Nos. 60/032,591, 60/032,592 and 60/032,593, all filed on Nov. 29, 1996, all of which are hereby incorporated by reference.

Figure 3:
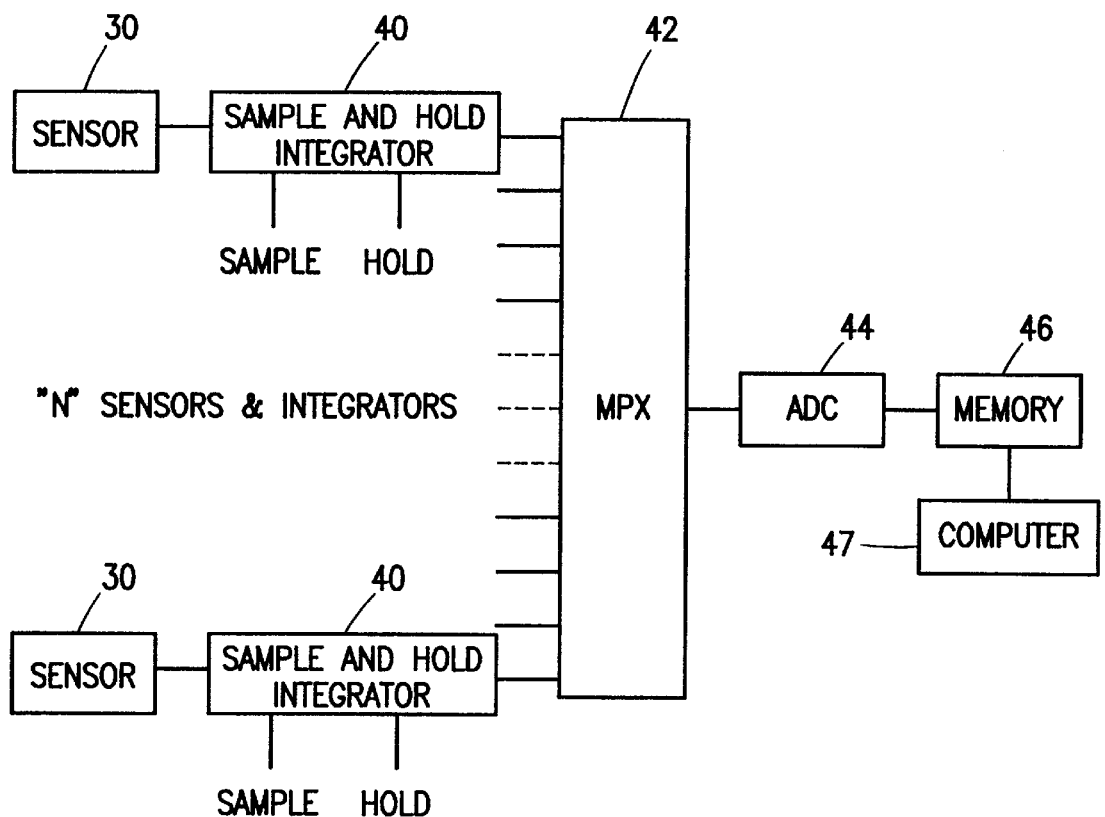
FIG. 3 is a block diagram of the signal processing system used in the present invention.

Each detector or sensor 30 is operably connected to its respective processing circuit 40, as best shown in FIG. 3. A multiplexer 42 is used to connect the respective integrator outputs to an analog-to-digital converter 44. The digitized individual detector or sensor response is stored in memory 46 for later use in image reconstruction by a computer 47. The circuit allows for simultaneous acquisition of data from all the detectors 30 at each angular position in the orbit of the scanning chamber 8. An example of the circuit 40 is further described in a copending application Ser. No. 08/979,328 filed on Nov. 26, 1997, claiming priority based on provisional application Ser. No. 60/032,590, filed on Nov. 29, 1996, both of which are hereby incorporated by reference. An improved embodiment of the circuit 40 will be discussed below.

Perimeter data of the object being scanned is obtained at each angular position in the orbit of the scanning chamber 8. Several methods are disclosed in copending application Ser. No. 08/965,148 filed on Nov. 6, 1997, claiming priority from provisional applications Ser. Nos. 60/029,897 and 60/029898 both filed on Nov. 8, 1996 and application Ser. No. 08/965,149 filed on Nov. 6, 1997, claiming priority from provisional application Ser. No. 60/029,898 filed Nov. 8, 1996, all of which are hereby incorporated by reference.

Preferably, a pair of sensor arrays 49 and lens 51 are disposed on the same side as the laser beam 16, as best shown in FIG. 2. The laser beam 16 impinges on the scanned object through the center 22 of the orbit. A bright spot is produced at point 18, which is reflected to the sensor arrays 49, represented by lines 53. At each distance from the orbit center, a specific element in the sensor array 49 will detect the bright spot. As the laser beam 16 and the rest of the scanner are orbited around the scanned object about the center, the output signal of the sensor array 49 will be in direct relationship to the perimeter of the scanned object. By acquiring data using one or more known diameters scanned objects, the level of the sensor signal can be calibrated with respect to the scanned object diameters. After calibration, the sensor signal can be electronically decoded to plot the coordinates for the perimeter of the scanned object as the scanner is orbited around the scanned object.

Each of the sensors 49 is a CCD sensor, such as CCD television pick up device, available from Texas Instruments, EGG and others, and includes lenses 51 to focus the rays 51 to the sensors. For the present invention, the sensor 49 is a linear, one dimensional CCD device, rather than the area 2-dimensional array used for television. The CCD sensor produces an analog signal corresponding to the light received along the line. A processing circuit 55 (shown in FIG. 8) can be implemented as an analog circuit, a digital hardware or in software running on a programmable device. An ADC (analog-to-digital converter) digitizes the video signal prior to processing by the computer.

It is advantageous to obtain the perimeter data during data collection of each slice to minimize error due to shifting of the object between slice positions. Perimeter data is used to calculate the chord lengths 20, which together with the corresponding detector data are used to reconstruct the image of the object. With the perimeter data, the chord lengths 20 at each scan position of the scanner 9 are known. Perimeter data consist of distances from the center of the orbit 22 to the point 18 at each angular position of the orbit.

Figure 4:
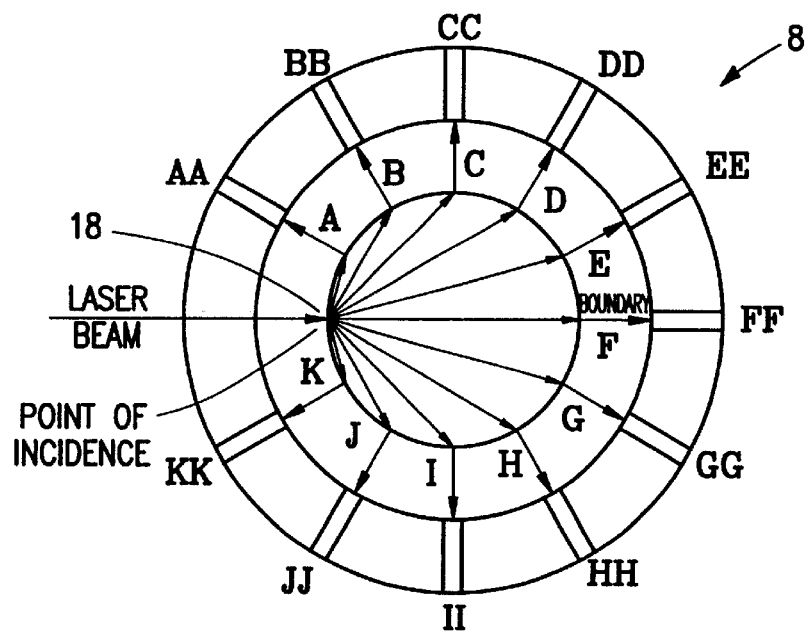
FIG. 4 is a schematic top view of the scanning chamber of FIG. 1, showing the geometric relationships between the impinging laser beam, chord paths through the object and the detector assemblies.
Figure 5:
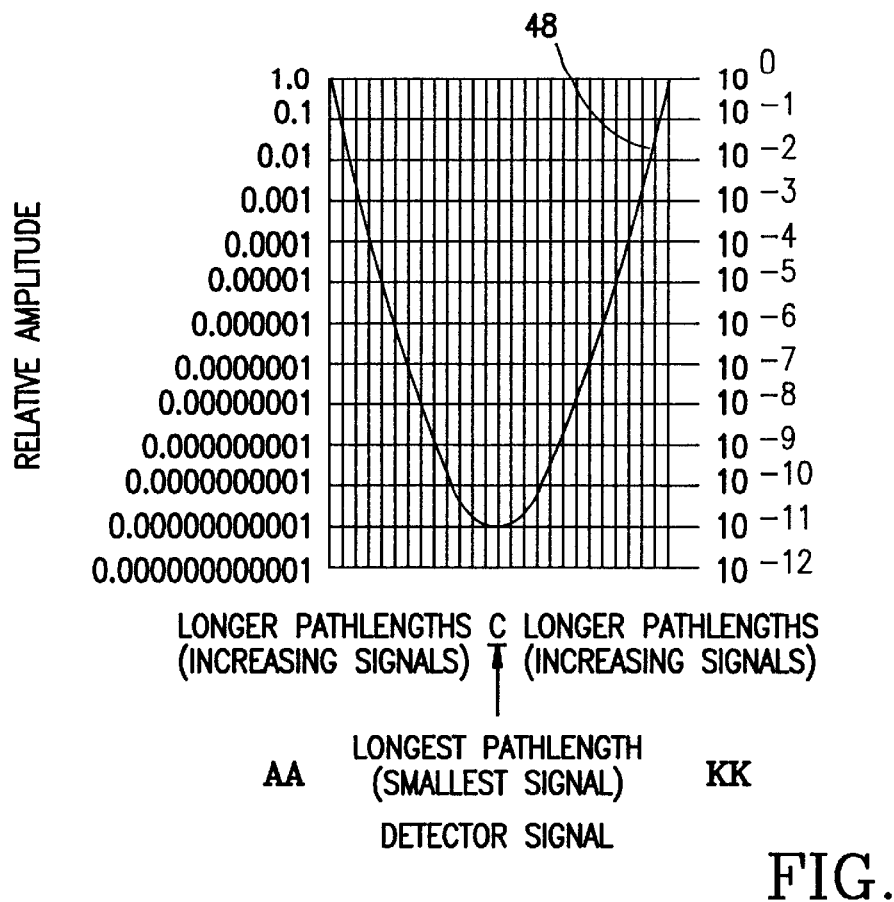
FIG. 5 is a graph of the relationship of the relative amplitude of detector signal and its corresponding chord path length through the object being scanned.

The scanner 9 is represented schematically in FIG. 4. The detectors 30 are designated as AA, BB , . . . , KK, indicating their respective positions along the arc. Optical path lengths taken by the laser beam through the object are represented as chords 18-A, 18-B , . . . , 18-K. At each angular position in the orbit 23, the relative amplitude of the detector signals at the detectors AA, BB , . . . , KK are generally indicated by the curve 48 shown in FIG. 5. The signals seen by the detectors AA and KK are strongest because of the shorter chord lengths 18-A and 18-K. The signal seen by the detector FF is smaller because of its corresponding longer chord length 18-F. It is therefore seen that the signal generally decreases from detectors AA to FF and increases from detectors FF to KK. Detector signal before amplication can range from $10^{-10}$ to 1 in relative amplitude.

Figure 6:
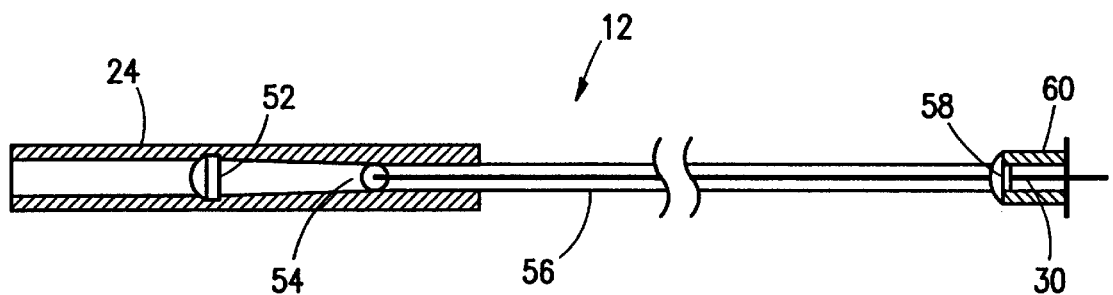
FIG. 6 is a detector assembly used in the present invention.

A preferred embodiment of the detector assembly 12 is disclosed in FIG. 6. A plano-convex lens 52 disposed within the housing 24 focuses the light unto a ball lens 54 which launches the light rays into a fiber optic cable 56. At the far end of the optic cable 56 is another plano-convex lens 58, which may be integral with the photodetector 30 disposed within an opaque housing 60. The fiber optic cable 56 is sufficiently long such that the detector 30 and its associated processing circuit 40 may be located remotely from the scanning chamber 8 and be sufficiently spaced from other detectors 30 to prevent electronic interference from each other.

Figure 7:
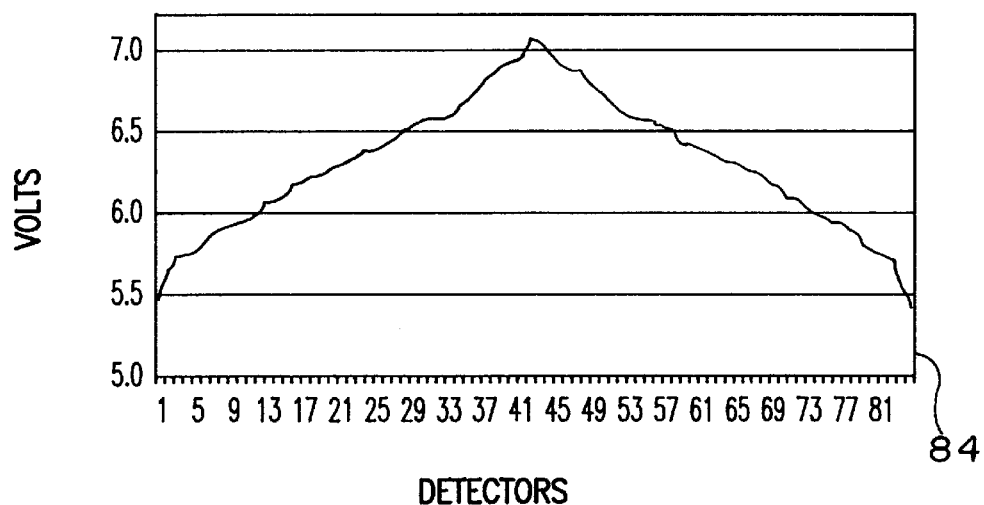
FIG. 7 is a graph of detector sensitivity relative to its geometric location for the scanner of FIG. 2 having 84 detectors.

In the present invention, 84 detector assemblies are used, although a different number is possible. The signal seen by each of the detector 30, depending on the physical location of housing 24 in the scanner 8, can vary approximately from $10^{-10}$ to 1.0 in relative amplitude. To accommodate this wide range, each detector assembly 12 is graded in terms of efficiencies and those with the highest efficiency are placed in the center of the detector array, such as detector position FF, with the longest path length through the breast and lower efficiencies assemblies are positioned where shorter optical path lengths through the breast are expected, such as detector position AA, as best shown in FIG. 7. With knowledge of the relative signal strengths as a function of location in the detector housing array and efficiency of the individual detector assemblies, the positioning of the detector assemblies 12 is implemented to use the highest efficiencies assemblies where the signal can reasonably be expected to be small.

The scanning apparatus 2 is disclosed schematically in FIG. 8. The output of the laser source 10 is a laser beam 62 directed to a beam splitter 64 to provide a laser beam 66 directed to a fiber optic cable 68 and another laser beam 70 directed to another fiber optic cable 72. The laser beam 66 as it emerges from the optic cable 68 is directed to another beam splitter 74 and emerges as a reduced power laser beam 16, and is directed into a lens collimator 78 (see FIG. 2). The lens collimator 78 controls the beam diameter of the laser beam 16. The second beam 80 from the beam splitter 74 is directed to a power monitoring diode 82 connected to a power monitoring circuit 84, using an amplifier and an analog-to-digital converter to produce a digital signal representing the power level of the laser beam 16. The laser beam 16 impinging on the breast 6 travels as optical chords 20 through the breast 6 and emerges at various locations 34 on the perimeter 19 of the breast, as best shown In FIG. 2. The housings 24 are optical collimators that limit the field of view to corresponding locations 34 on the perimeter of the breast 6. The light that enters each of the housings 24 is transmitted through the fiber optic cable 56 and impinges on the detector 30 at the other end of the fiber optic cable 56.

Each of the detectors 30 is coupled to the sample and hold integrator circuit 40, the output of which is coupled to the multiplexer 42, which is connected to the analog-to-digital converter 44, and which is connected to the computer 47.

The laser beam 70 emerging from the fiber optic cable 72 is coupled to a photo-detector 102, which develops a signal used by a laser synchronization circuit 104, which generates an electronic pulse each time the laser source 10 produces a pulse of power. The arrival time of the laser pulse at the detector 102 and hence the time at which the laser synchronization pulse is generated is controlled by the length of the fiber optic cable 72. Fine tuning of the time of occurrence of the laser synchronization pulse is provided by a time delay circuit 106, which produces a delayed signal. The time delay circuit 106 may be implemented with a few feet of cable. The time delay laser synchronization pulse is used as one input to a high speed time-gated electronic switch control circuit 108. The computer 47 also provides a delay control signal to the control circuit 108. A laser pulse counter 110 is controlled by the computer 47 to provide a signal to the circuit 40 to control the integration time that occurs within the circuit, as will be further discussed below.

Figure 9A:
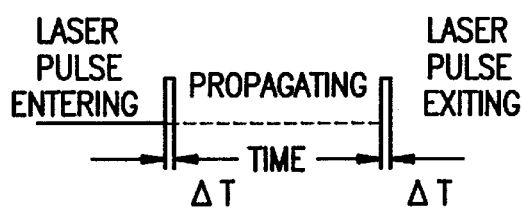
FIG. 9A is a representation of a propagating laser pulse through a non-attenuating medium.
Figure 9B:
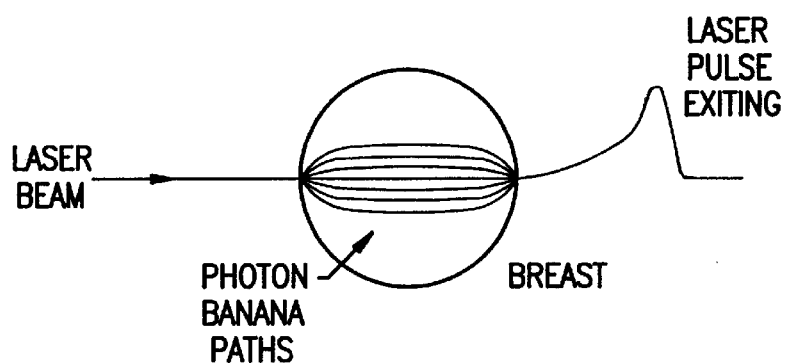
FIG. 9B is a representation of various paths, called photon banana paths, the laser pulse takes traveling through the breast.

Referring to FIG. 9A, a laser pulse propagating through a non-attenuating medium such as air will travel in a straight line. A laser pulse directed into a breast does not follow a straight-line propagation path, best shown in FIG. 9B. Breast tissue causes the photon beam to scatter, resulting in a zig-zag-like course through the breast. The zig-zag-like course in 2- or 3-dimensional space is referred to as a banana path. Referring to FIG. 9, square wave laser pulse after traversing through the breast will emerge with a general shape shown. Because all of the photons do not follow the same path, the measured photon intensity at the measurement point on the surface of the breast is time dependent. A small number of photons arrives first, followed by photons that have traveled a longer path, and lastly followed by the photons that have taken the longest path through the breast. The early arriving photons are used in image reconstruction.

A detector with high-speed response characteristics can be used to display the photon-intensity versus time plot, called the Temporal Point Spread Function (TPSF) curve, of a laser pulse transmitted through the breast. A TPSF curve of a laser migrating through a media is disclosed in FIG. 10. The TPSF curve can be fitted to the diffusion equation. After curve fitting, the diffusion equation can be used to determine the optical characteristics of the breast, such as the absorption coefficient, $\mu_a$, the transport scattering coefficient, $\mu_{s'}$, and the index of refraction, η, can be calculated. Portion 111 of the curve represents photons that are among the earliest to emerge from the breast and thus have undergone the least amount of scattering. The earliest arriving photons represented by the portion 111 of the curve are used in image reconstruction. Portion 113 represents photons that are highly scattered and are not used in image reconstruction.

Figure 10:
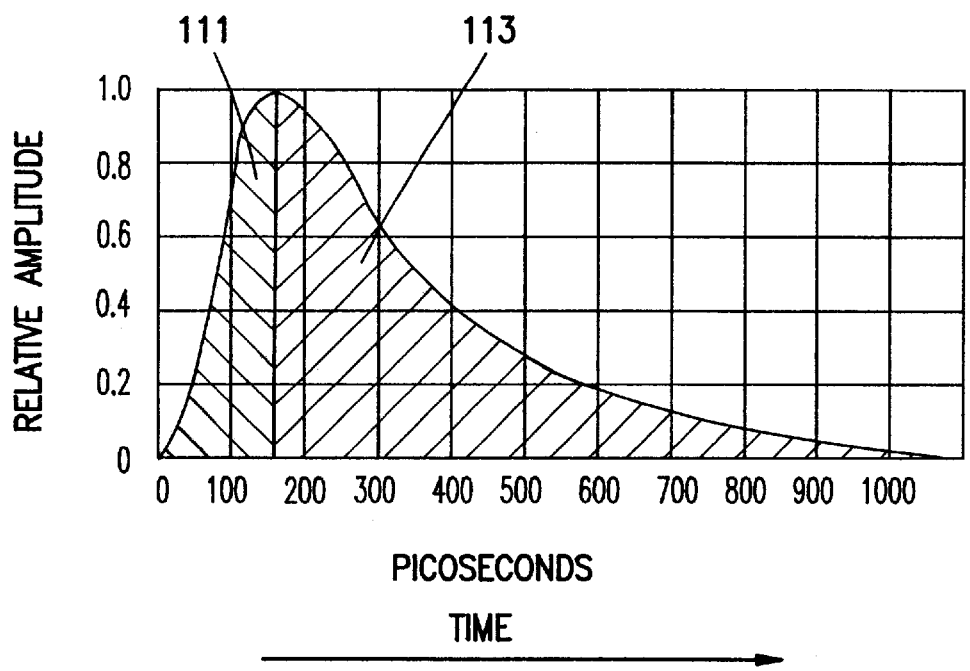
FIG. 10 is a response curve of a high-speed photodetector illuminated by a laser pulse after that has traveled through the breast.

For a detector circuit having response characteristics shown in FIG. 10, its rise-time, the time required for the amplitude starting at 10% peak value to reach its 90% peak value, is approximately 300 picoseconds (ps). From this, the approximate bandwidth of the detector circuit would be $0.35/300$ ps or 1.2 GHz.

Figure 11:
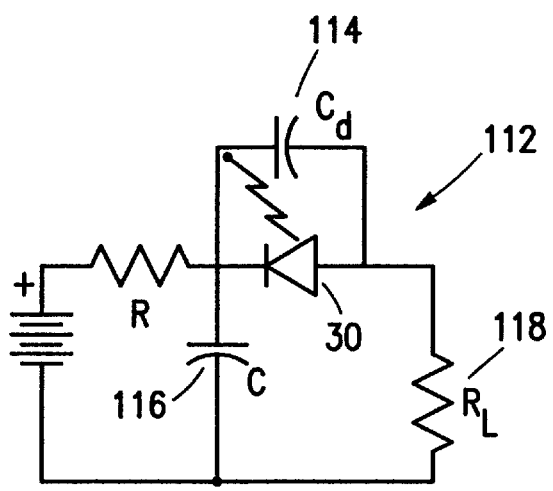
FIG. 11 is a schematic diagram of photodetector circuit used in the present invention.

In a detector circuit 112 used in the present invention, as shown in FIG. 11, the photodetector 30 is reversed biased to reduce the photo-diode capacitance, represented by capacitor 114. Capacitor 116 decouples the photo-diode 30 from the bias supply. Current flow in the diode 30 begins a few picoseconds after the photons begins impinging on the photo-diode. The combined capacitance, comprising of the junction capacitance, package capacitance and stray wiring capacitance, and the load resistance 118 determine the rise-time of the overall circuit. For high frequency applications, the load 118 is preferably 50 ohms. For a photo-diode with a capacitance of 1 pf, the rise-time is calculated as follows, $$t_r = 2.2 R_L C_d = 2.2(50 \text{ ohms}) (1 \times 10^{-12} f) = 110$$

The approximate frequency response of the photo-diode circuit is, $$0.35/110 \times 10^{-12} = 3.2 \text{ GHz}.$$

High speed photodetectors with a capability to capture the waveform of a fast light-pulse, such as that shown in FIG. 10, are available today. Advances in photo-detector technology have produced photodetectors with small size active areas resulting in low capacitance.

Figure 12A:
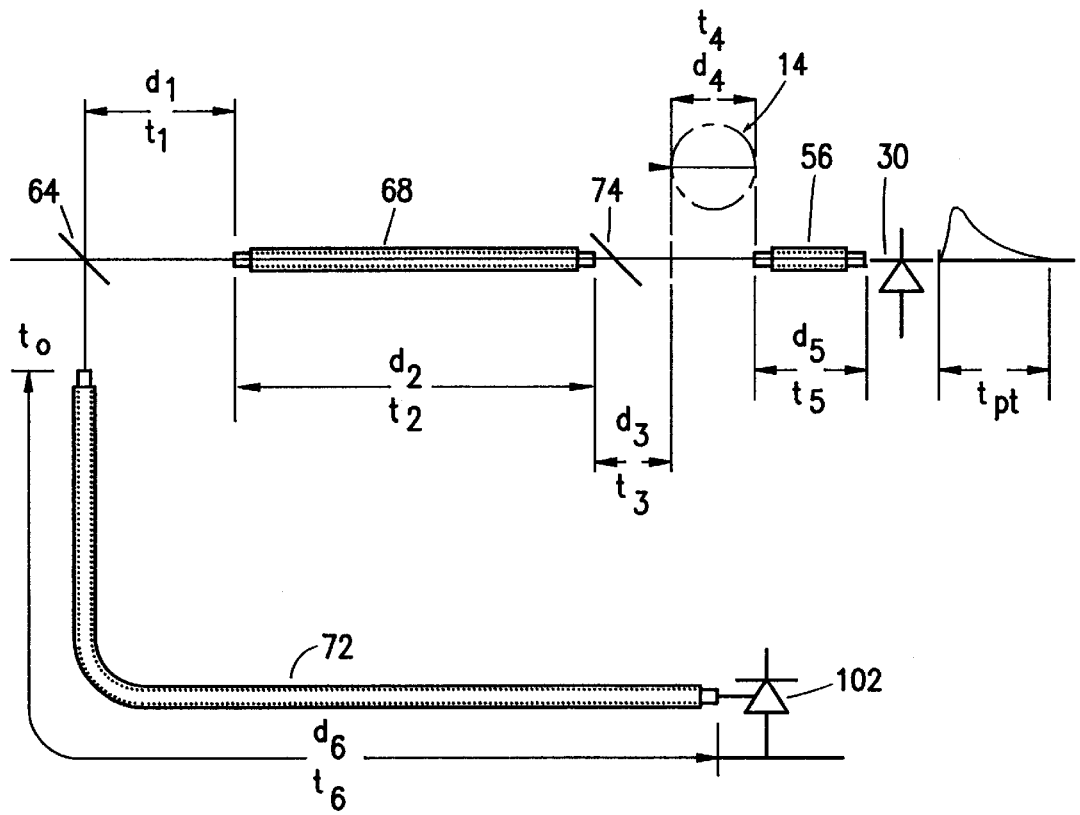
FIGS. 12A and 12B are schematic representations of the time of travel for a laser pulse going through the breast and a synchronization pulse going through a parallel path.

The propagation of a laser pulse through the scanning apparatus 2 will now be described. The point in time at which the laser pulse will arrive at the detector 30 after passing through the breast can be calculated. Referring to FIG. 12A, in a path starting at the beam splitter 64 and going through the fiber optic cable 68, distances that a laser pulse would traverse up to the point it exists the breast are known, indicated as $d_1$, $d_2$, $d_3$, $d_4$ and $d_5$. The distance $d_4$ is known from the perimeter data of the breast. The corresponding time periods $t_1$, $t_2$, $t_3$, $t_4$ and $t_5$ can be calculated from the known distances and the known speed of light in air, the fiber optic cable 68 and the breast. The speed of propagation of the laser pulse through the breast can be approximated. The nominal value of the index of refraction, $\eta$, of the breast tissue is 1.54. The speed of light in the breast, $C_b$, can be calculated as follows, $$C_b = \text{speed of light in a vacuum}/\eta, \text{ index of refraction},$$

$$C_b = 3 \times 10^8 \text{ m/s}/1.5 = 2 \times 10^8 \text{ m/s}.$$

With the chord length having been determined previously from the perimeter data, then the time of propagation $t_4$ through the breast is, $$t_4 = \text{chord length}/C_b.$$

The laser pulse as it emerges from the breast will then travel through the fiber optic cable 56 and then impinge on the detector 30. The known distance of the fiber optic cable 56 is $d_5$ and the corresponding time of travel through it is $t_5$. The duration length of the TPSF curve is indicated as $t_{pt}$.

Figure 12B:
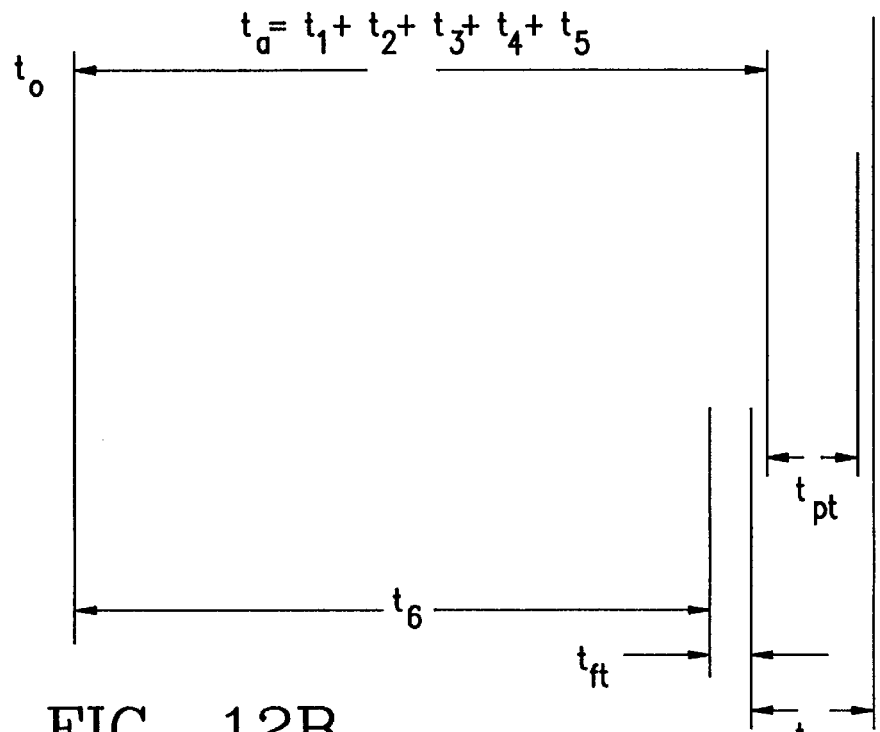

The time of propagation $t_6$ of the laser pulse from the beam splitter 64 through the fiber optic cable 72 can be calculated from the known length $d_6$ of the cable 72. The time $t_6$ can be adjusted by lengthening the fiber optic cable 72 to delay the arrival of the laser pulse at the photodetector 102 or by shortening the length of the fiber optic cable 72 to shorten the arrival time. The time $t_6$ is configured to be just short of the time for the laser pulse to reach the detector 30, as best shown in FIG. 12B.

The output of the photodetector 102 is used by the laser synchronization circuit 104 to generate a pulse each time a laser pulse is detected by the photodetector 102. The time at which the synchronization pulse is generated may be fine tuned by an amount $t_{ft}$ by the time delay circuit 106, which generates a delayed pulse. The laser synchronization pulse is used as one input to the high speed time-gated electronic switch control circuit 108. The output of the circuit 108 is controlled by the computer 47.

The time-gating signal of the circuit 108 is adjusted approximately in 17 picosecond increments over approximately a 17 nanosecond period, which is approximately the width of the TPSF curve. Referring to FIG. 12B, the expected arrival of the laser pulse at the detector 30 is $t_a$, using t=0 starting at the beam splitter 64. The expected time of arrival of the synchronization laser pulse at detector 102 is $t_6$. The time delay circuit 106 introduces a time delay to fine tune the synchronization pulse at $t_{ft}$, which is just before time $t_a$. The time period $t_g$ for sampling the TPSF curve starts just before the beginning of $t_{pt}$ and after the end of $t_{pt}$, thus bracketing the duration length of the TPSF curve.

Figure 13:
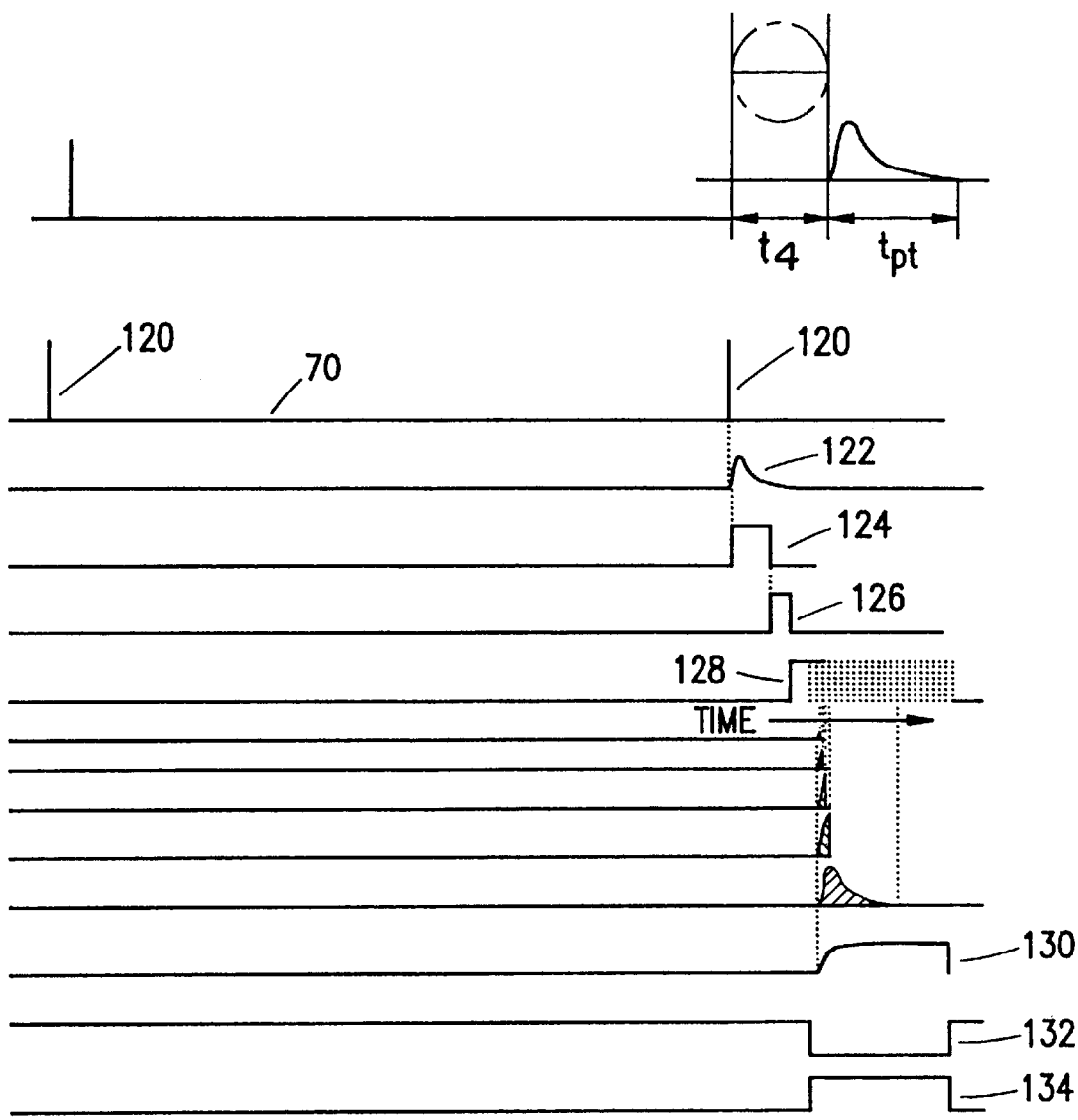
FIG. 13 is shows the relative electronic signals in the scanner.

Referring to FIG. 13, the relative electronic timing of signals is disclosed. The laser beam 70 propagating through the fiber optic cable 72 includes laser pulses 120 which generate a signal 122 at the laser synchronization detector 102. The synchronization circuit 104 generates a signal 124, which causes the time delay 106 to generate the time delayed signal 126. The signal 126 initiates a time-gating signal 128, which is adjusted in approximately 17 picoseconds over approximately a 17 nanosecond period by means of a programmable delay chip controlled by the computer 47, as will be discussed below. The time-gating signal 128 samples a portion of the TPSF curve that will be coupled to an integrator in the circuit 40. The input to the integrator is the selected portion of the TPSF curve. The integrator generates a signal 130. The integrator is also controlled by a hold signal 132 and a reset signal 134.

Figure 14:
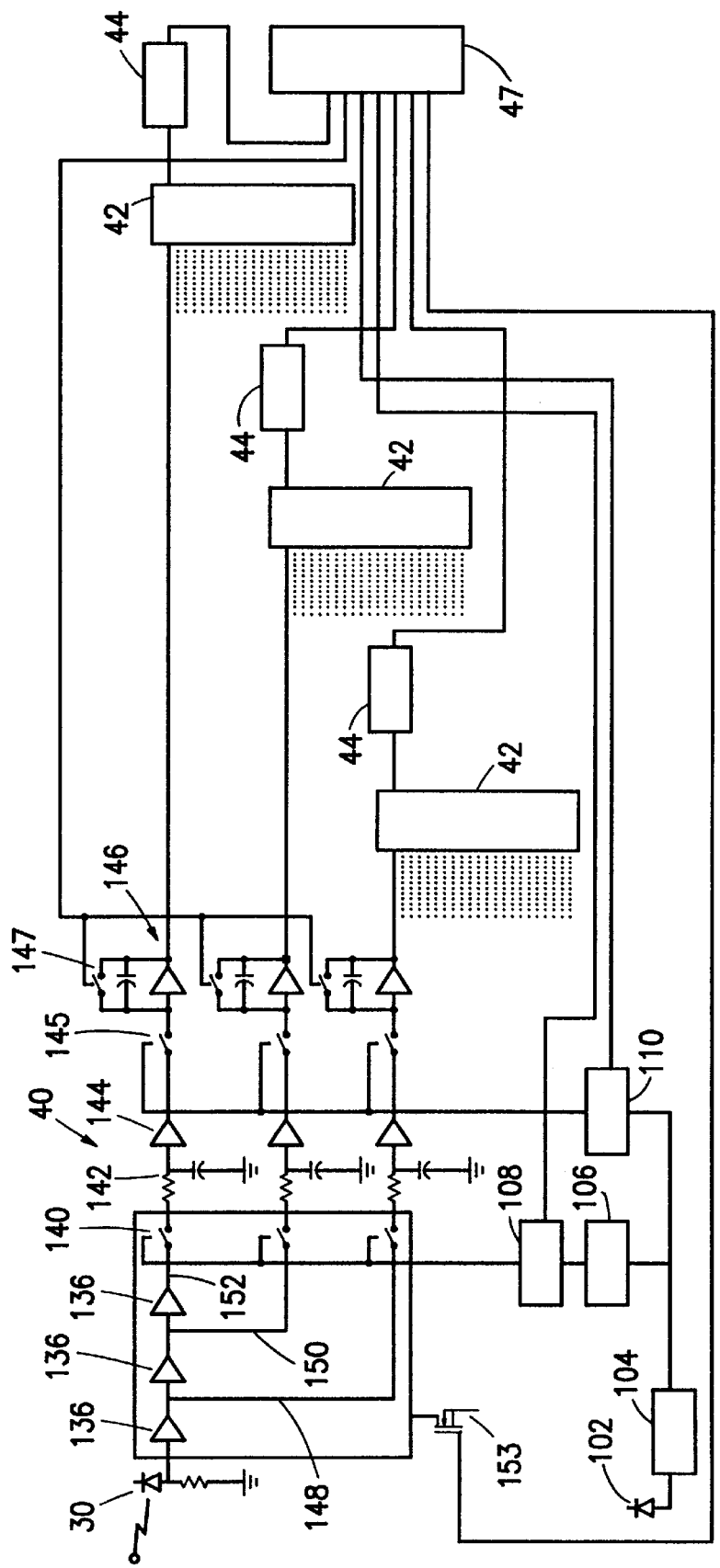
FIG. 14 is a schematic diagram of a processing system for the photodetector signal, showing three amplification stages to accommodate the dynamic range of the detector output.

A schematic diagram of the signal processing circuit 40 is disclosed in FIG. 14. The circuit 40 provides three different amplitudes for the detector signal of detector 30. The output of each high frequency linear pre-amplifier 136 is coupled to high speed time-gated electronic switch 140, RC network 142, an amplifier 144 and an integrator 146. The integrator 146 includes a hold switch 145 and a reset switch 147.

The circuit 40 is configured to have a low-gain stage 148, a medium-gain stage 150 and a high-gain stage 152. The three gain stages are designed to accommodate the large dynamic range of detector signals available for detection that can range from $10^{-10}$ to 1 in relative amplitude.

A high speed electronic switch 153 is advantageously used to disconnect the power to the pre-amplifiers 136 and the high speed time-gated electronic switches 140 to achieve a substantial reduction in the amount of power used by the circuit between laser pulses.

Figure 15:
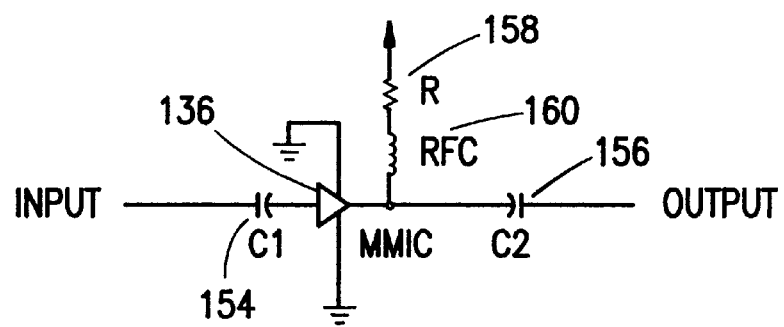
FIG. 15 is a schematic diagram of a monolithic microwave integrated circuit amplifier used in the present invention.

The high frequency linear pre-amplifier 136 is known as a monolithic microwave integrated circuit (MMIC), which is a radio frequency amplifier specifically designed to have exceptional performance at high RF frequencies. The MMIC 136 itself is a single component with four electronic connections; namely, an input terminal, an output terminal and two ground connections, as best shown in FIG. 15. An input capacitor 154 is used to AC couple an input signal to the MMIC. An output capacitor 156 is used to AC couple the amplified output signal to the next stage of the circuit. Resistor 158 is used to set the operating points for the device by producing a voltage drop to establish a DC voltage at the output terminal of the MMIC. A choke 160 is used to decouple the resistor 158 from the MMIC. The capacitors 154 and 156 are critical to optimal circuit performance of the MMIC. At GHz frequencies at which the MMIC operates, microwave capacitor with package construction that minimizes lead-inductance must be used. The MMIC's are selected for the gain they produce and their useful operating frequency range. MMIC's are available from Mini-Circuits, models ERA-1 and ERA-5, which are used in the present invention.

Referring to FIGS. 16A, 16B, 16C and 16D, the RC filter 142 stretches the width of a sample signal 155 to produce a stretched signal 157 which is then amplified by the amplifier 144 to produce an amplified signal 159 to allow the integrator 146 to produce a larger detector signal. Since time gating has controlled the sampling of the signal 155, stretching the width of the signal 155 after sampling to become signal 157 followed by the amplifier 144 does not defeat the sampling process but provides a wider window of time for the integrator 146 to integrate. The stretching feature is a key function that advantageously allows fewer laser pulses to be used for any one measurement and advantageously reduces the time required to perform a scan.

Figure 17:
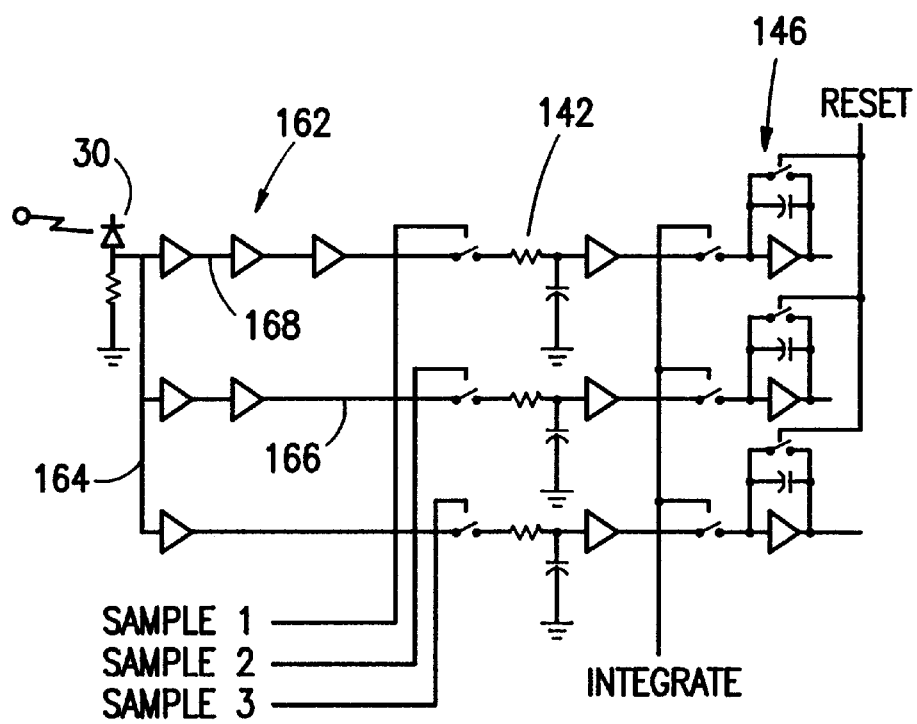
FIG. 17 is another embodiment of a processing circuit for amplifying the output of the photodector.

Another embodiment for the circuit 40 is disclosed in FIG. 17 as circuit 162. The output of each detector 30 is directly connected to three gain stages, namely, a low-gain stage 164, a medium-gain stage 166 and a high-gain stage 168. Samples switches 140 are individually controlled.

Figure 18:
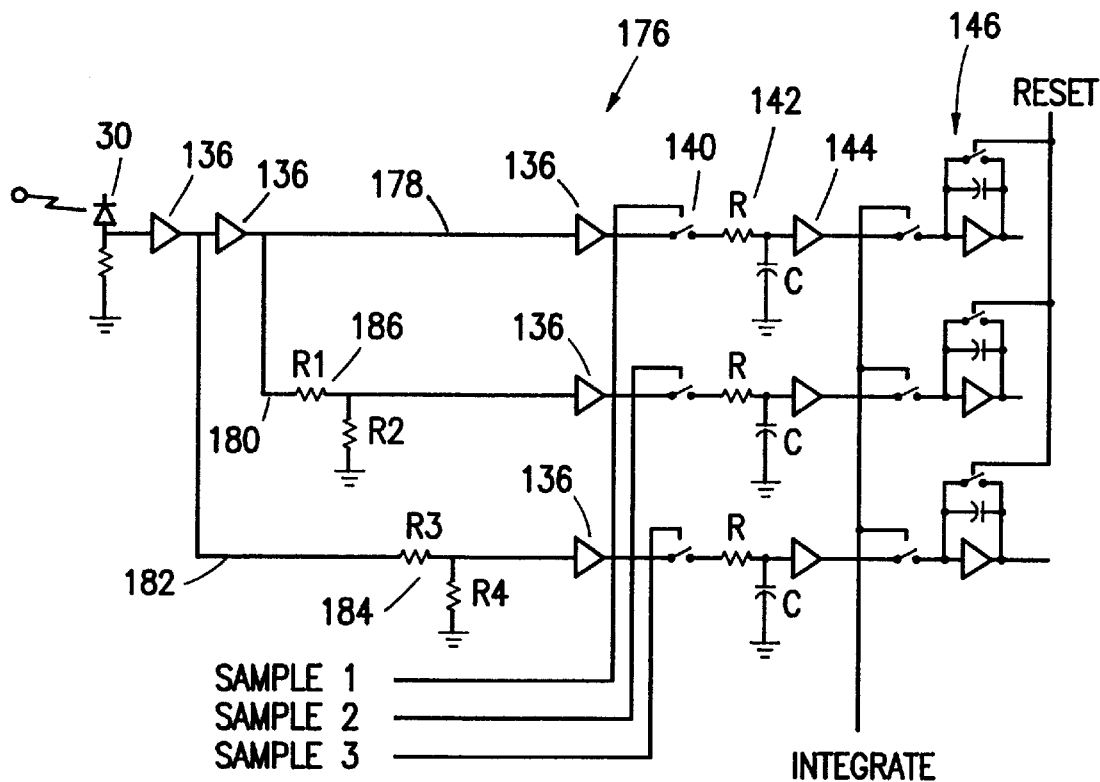
FIG. 18 is another embodiment of a processing circuit for amplifying the output of the photodetector.

A preferred embodiment of the signal processing circuit 40 is circuit 176, as best shown in FIG. 18. The circuit 176 has a high-gain pre-amplifier stage 178, a medium-gain pre-amplifier 180 and a low-gain pre-amplifier stage 182. The high-gain pre-amplifier stage 178 consists of three cascaded MMIC pre-amplifiers 136 with an overall gain equal to the product of the gains of the respective MMIC's.

The overall gain of the low-gain pre-amplifier stage 182 is the product of the respective gains of the two MMIC pre-amplifier 136 and the attenuation provided by the resistive circuit 184. The overall gain is set to one.

The overall gain for the medium-gain pre-amplifier stage 180 is the product of the gains of the three respective MMIC pre-amplifiers 136 and the attenuation provided by the resistive circuit 186. The values of the resistors in the resistive circuit 186 are chosen such that the overall gain for the medium-gain pre-amplifier stage 180 is equivalent to the overall gain of two cascaded MMIC pre-amplifiers.

Figure 19:
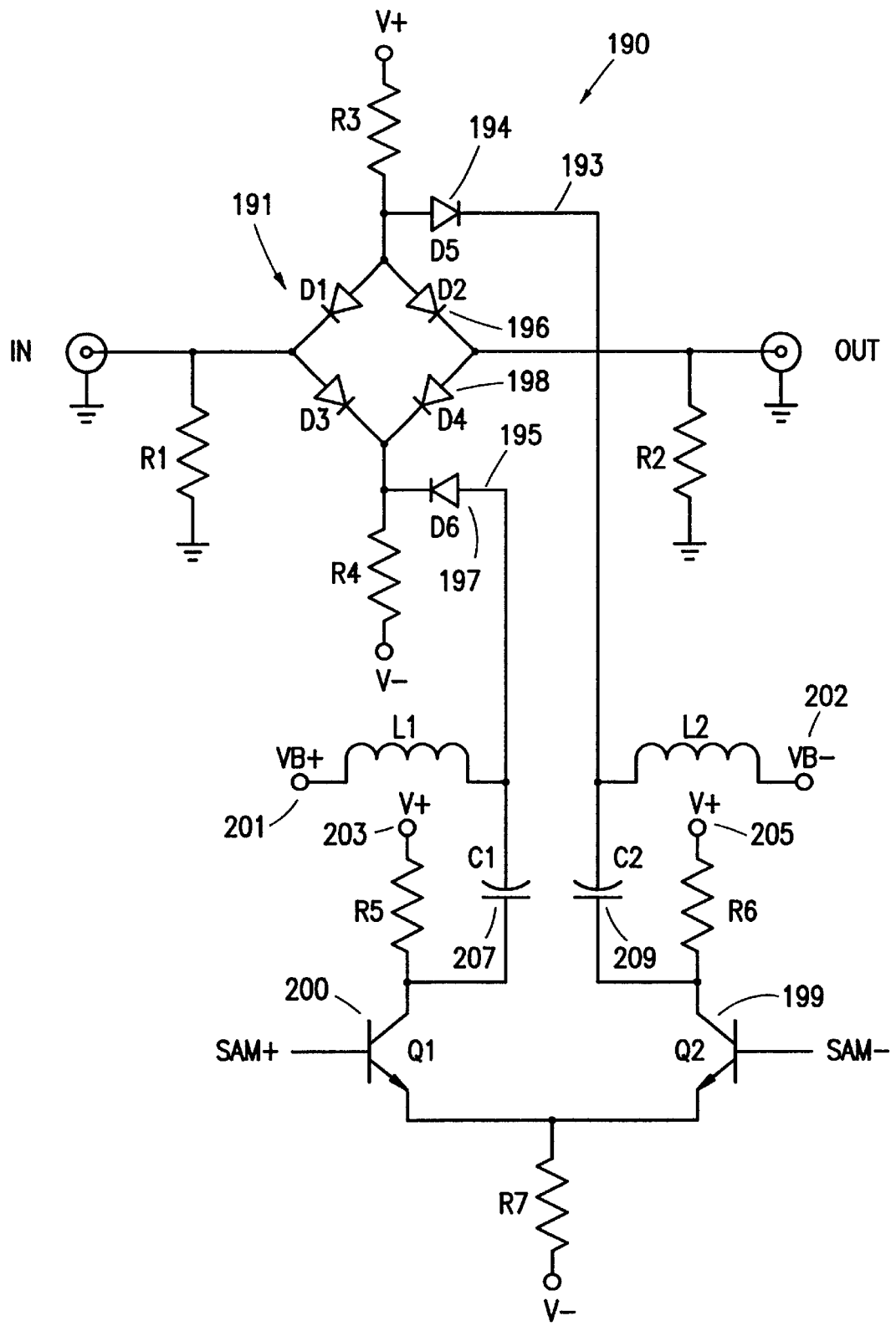
FIG. 19 is a schematic diagram of a high-speed switch used in the present invention.

The sampling switch 140 is implemented as a diode-bridge switch 190, as disclosed in FIG. 19. The diode-bridge switch 190 switches at a very high speed to accommodate the 17 picoseconds sampling intervals. However, the switch produces a switching transient signal and DC offset that appears as an input signal on the output of the MMIC providing the desired signal to the bridge. In the preferred circuit 176, the reflected signal from the switch 190 is advantageously attenuated as it passes through the MMIC pre-amplifiers 136 in the low and high medium pre-amplifier stages 180 and 182 and by the 50-ohm characteristics input impedance of the MMIC and the resistive circuits 184 and 186. The reflected signal is undesirable, since the reflected signal can be larger than some detector signals.

In the circuit 168, the transient reflected signal from the diode-bridge switch appears as an input to high-gain pre-amplifiers stage 168. Although the reflected signal is attenuated by approximately a factor of 10, it is amplified by approximately a factor of $10^3$ by the three cascaded MMIC pre-amplifiers 136. The DC offset of the reflected signal causes the high-gain pre-amplifier stage integrator 140 to rapidly integrate to one power supply rail.

Referring back to FIG. 19, the switch 190 includes a diode bridge circuit 191, commonly used as a RF switch to sample a (temporal) portion of a waveform, as in a sampling oscilloscope. The diode bridge circuit 191 is turned on and off by voltage sources at line 193 and 195, acting respectively through diodes 194 and 197. To close the switch, the voltage at line 193 would be at a positive voltage, backbiasing diode 194 and the voltage at line 195 at a negative voltage, backbiasing the diode 197. Thus, all the bridge diodes will be conducting and the signal at the input IN will appear at the output OUT.

With the voltage at line 193 at a negative voltage and the voltage at line 195 at a positive voltage, diodes 196 and 198 will be backbiased, isolating the output OUT from the input IN. Typically, the voltages at lines 193 and 195 will be mirror-image waveforms.

The voltages at lines 193 and 195 are provided by the signals SAM, which are differentials ECL, normally false. Thus, transistor 199 is normally on and transistor 200 is off. The bias voltages 201 and 202 are set to be slightly larger than the largest input signal, but significantly smaller than voltages 203 and 205. The diode bridge circuit 191 is normally off with the diodes 194 and 197 conducting.

To sample the input, SAM+ is driven high and SAM− is driven low simultaneously. Transistor 200 turns on and transistor 199 turns off. Coupled through capacitors 207 and 209, diodes 194 and 197 are driven to a backbiased state. The diode bridge circuit 191 now conducts the input to the output.

Figure 20:
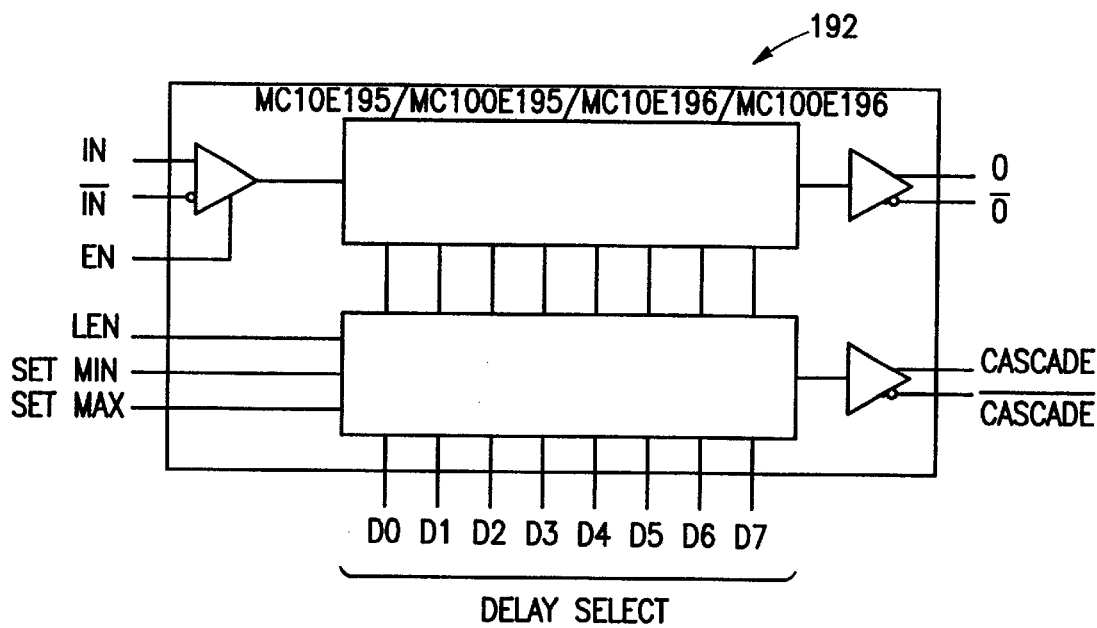
FIG. 20 is a block diagram of a programmable delay chip used in the present invention.
Figure 21:
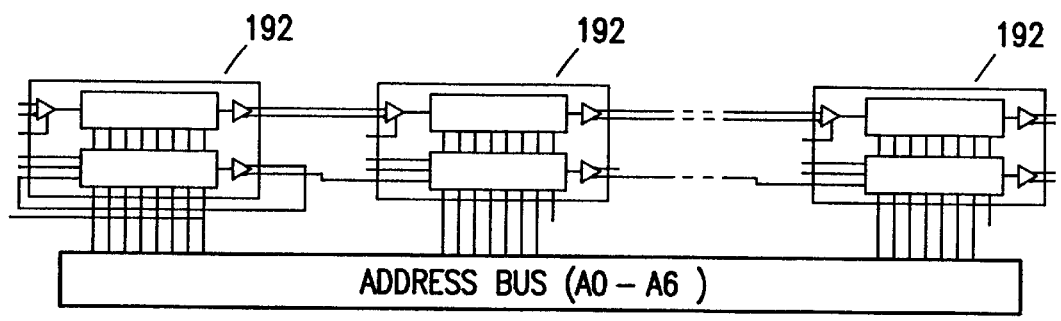
FIG. 21 is a block diagram of a plurality of programmable delay chips cascaded together for increased number of delay intervals.
Figure 22A:
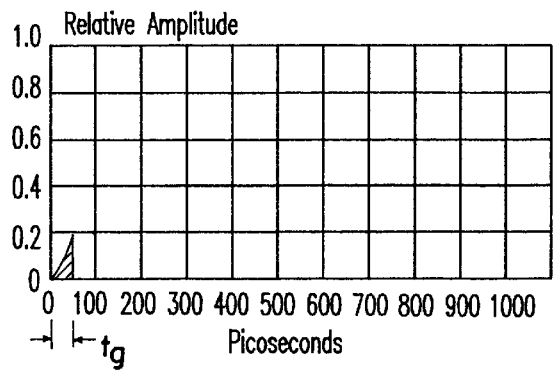
FIGS. 22A, 22B, 22C, 22D and 22E shows the extent of the TPSF curve that is sampled using successively longer time-gate period.
Figure 22B:
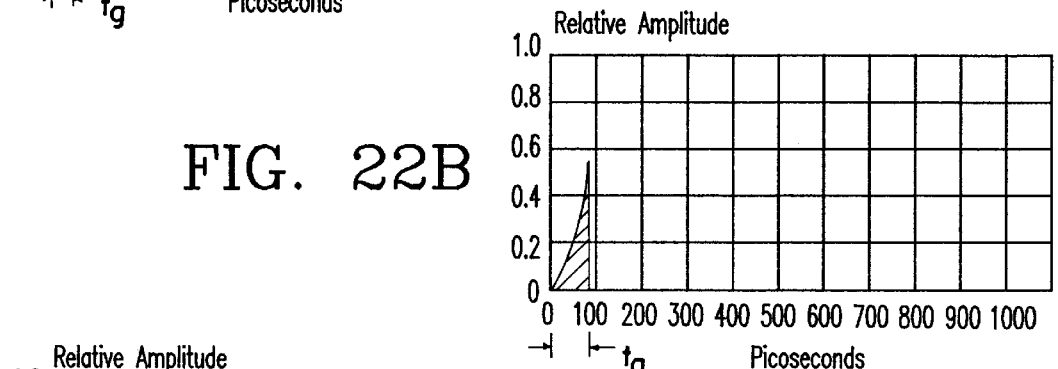
Figure 22C:
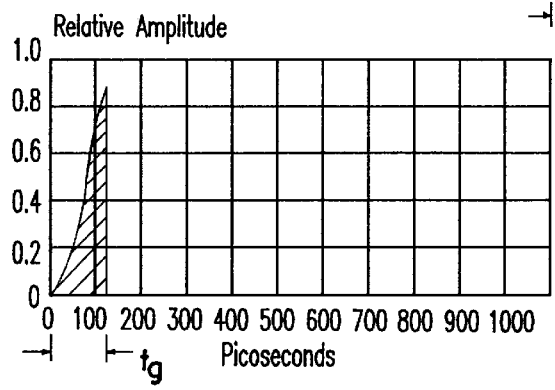
Figure 22D:
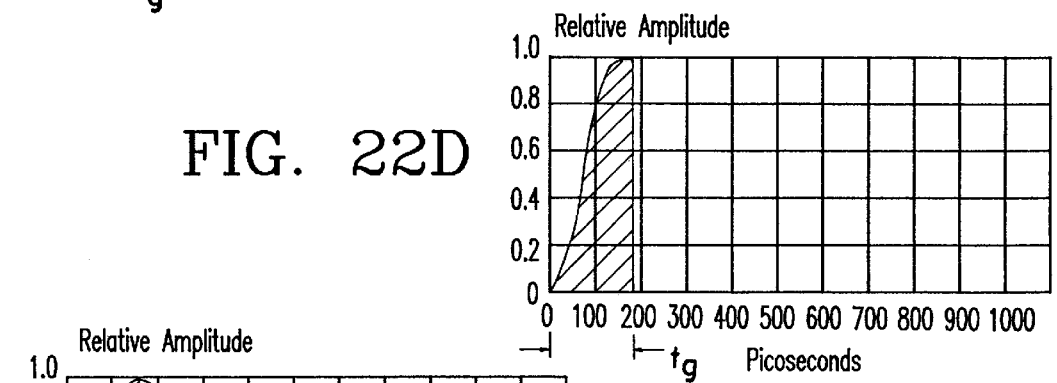
Figure 22E:
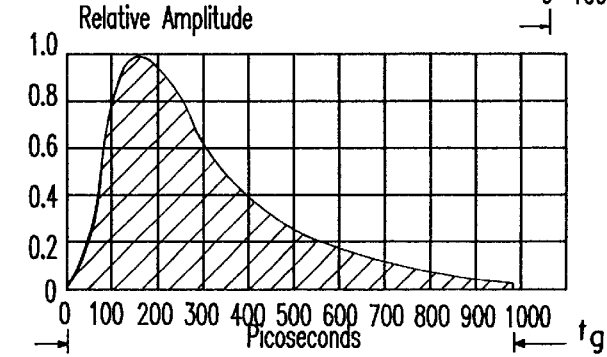

The electronic switch control circuit 108 is implemented by a programmable delay chip 192, as best shown in FIG. 20. The programmable delay chip 192 is made by Motorola, model no. MC10E195-MC100E195. Model No. MC10E196-MC100E196 can also be used. The programmable delay chip 192 is designed to produce a series of delays 17 picoseconds part. Several programmable delay chips 192 may be cascaded to provide the required time delays, as best shown in FIG. 21. The present invention uses eight programmable delay chips to sample the entire TPSF curve at approximately 17 picosecond intervals. This will provide 1024 sampling steps for a TPSF curve as long as 17 ns for the longest expected chord length through a large breast.

The portion of the TPSF data that is sampled in the $t_g$ interval is selectable at approximately 17 picoseconds steps over a 17 nanosecond window. Preferably, the sampling intervals are 8 blocks of 17 ps intervals.

Electronic control of the delay time is provided by the programmable delay chip 192. Since the detector signals are small, multiple laser pulses, preferably 5, are used to develop a larger signal. Three different numbers of laser counts are used to develop an ever increasing signal, since there is no way of knowing the amplitude of the signal that would be experienced. Thus, for any one time-gate interval, groups of 8, 16 and 32 laser pulses might be collected. The laser pulse numbers can be set in interval values ranging from 1 to 128 pulses. After a preset number of laser pulses has been sampled, the next time-gate is set to sample along the portion of the TPSF curve. The length of the TPSF curve is also not known and actually changes as different portions of the breast are scanned. A longer chord through the breast produces a longer TPSF curve with a decreasing leading edge time. The time delay intervals and the total width of the period of time required to capture the entire TPSF is not known ahead of time. The laser-pulse counting and incrementing of the time-gate delay is repeated until the available range of values has been covered. The result of this form of data collection is to attempt to acquire data that will cover a considerable number of variables that are encountered in actual in-vivo scanning. For example, one acquired data contains approximately 16 mega bytes of data.

The computer 47 sets the time-gate delay signal to select how much of the TPSF data will be used. A computer command sets the number of laser pulses that would be used by the integrator 146. The laser pulse counter is incremented by each laser synchronization pulse generated by the circuit 104. The number of laser pulses that will be used is set into the laser pulse counter 110 by the computer 47.

FIGS. 22A–22E illustrate the sampling of a TPSF curve as the time-gate delay $t_g$ is incremented to progressively sample the curve. Since $t_a$ is known (see FIG. 12B), the high speed time-gated electronic switch 140 is electronically closed at a time preceding $t_a$. The time the high speed time-gated electronic switch 140 is electronically closed is determined by the computer 47 and the circuit 108. This technique advantageously detects photons that are among the earliest to emerge from the breast and thus has undergone the least amount of scattering. The early arriving photons are used in image reconstruction described in copending application Ser. No. 08/979,624, claiming priority from provisional application Ser. No. 60/032,594, filed on Nov. 29, 1996, both of which are hereby incorporated by reference.

The characteristics of the laser beam used in the present invention are important. Theoretical calculations and physical experiments have confirmed that at 790–800 nm wavelength range, a 3 mm diameter, 500 milliwatt average power, $P_{avg}$, laser beam with a pulse width, PW, of 110 femtosecond (fs) at a repetition rate, RR, of 82 MHz causes no biological damage.

The power per square centimeter, $P_{cm2}$ is calculated as:

$$\text{Area of beam} = \pi R^2 = \pi (3/2 \text{ mm})^2 = 0.0706 \text{ cm}^2$$

$$P_{cm2} = (1/0.0707 \text{ cm}^2) \times 500 \text{ mW}$$

$$= 7.07 \text{ W/cm}^2$$

The energy per pulse, $E_{pp}$ is calculated as:

$$E_{pp} = P_{avg}/RR = 500 \text{ mW}/8.2 \times 10^7$$

$$= 6.095 \times 10^{-9} \text{ J}$$

$$\approx 6.1 \text{ nJ}$$

The peak power, $P_p$, is calculated as:

$$P_p = E_{pp}/PW = 6.1 \text{ nJ}/110 \text{ fs}$$

$$= 6.1 \times 10^{-9}/1.1 \times 10^{-13}$$

$$= 55,454.5 \text{ W} = 55.5 \text{ kW}$$

In the present invention, peak power per pulse is not of significance, but energy per pulse is because energy per pulse determines the number of photons that are available for imaging. The quantum energy of a photon, e, is calculated as follows:

$$e = hf$$

where h=6.6252×10$^{-34}$ Js, Planck's constant, and f=the frequency=c/$\lambda$.

where c=3×10$^8$ meter per second and $\lambda$=800 nm $$e = 6.6252 \times 10^{-34} \text{ Js} \times (3 \times 10^8 \text{ m/s}/8 \times 10^{-8} \text{ m})$$

$$= 2.48 \times 10^{-18} \text{ J per photon}$$

The energy per pulse was calculated above as 6.097×10$^{-9}$ J. The number of photons per pulse is calculated as follows $$\text{Number of photons per pulse} = \text{energy per pulse}/\text{energy per photon}$$

$$= 6.1 \times 10^{-9} \text{ J}/2.48 \times 10^{-18} \text{ J}$$

$$= 2.44 \times 10^{10}$$

If an attenuation factor of 10$^8$ or 10$^{10}$ is considered, it is clear that few photons would be available for imaging, especially when the scattering of the photon beam is considered. It has been experimentally determined that the energy per pulse required for medical optical imaging is on the order of 100 to 500 $\mu$J. The number of photons per pulse is calculated as follows:

Number of photons per pulse=energy per pulse/energy per photon

@100 $\mu$J, $$\text{Number of photons per pulse} = 1 \times 10^{-4} \text{ J}/2.48 \times 10^{-18} \text{ J}$$

$$= 4.03 \times 10^{13}$$

@300 $\mu$J, $$\text{Number of photons per pulse} = 3 \times 10^{-4} \text{ J}/2.48 \times 10^{-18} \text{ J}$$

$$= 1.2 \times 10^{14}$$

The repetition rate of the laser 10 must be low enough to prevent adverse physiological reactions. If the average power is held constant and the energy is known, then the repetition rate can be calculated as follows:

$$@ \ 100 \ \mu J, RR = P_{avg}/E_{pp}$$

$$= 500 \text{ mW}/100 \ \mu J = 0.5 \text{ W}/1 \times 10^{-4} \text{ J}$$

$$= 5,000 \text{ pulses per second}$$

$$= 5 \text{ kHz}$$

$$@ \ 300 \ \mu J, RR = P_{avg}/E_{pp}$$

$$= 500 \text{ mW}/300 \ \mu J = 0.5 \text{ W}/1 \times 10^{-4} \text{ J}$$

$$= 1,667 \text{ pulses per second}$$

$$= 1.7 \text{ kHz}$$

$$@ \ 500 \ \mu J, RR = P_{avg}/E_{pp}$$

$$= 500 \text{ mW}/500 \ \mu J = 0.5 \text{ W}/1 \times 10^{-4} \text{ J}$$

$$= 1,000 \text{ pulses per second}$$

$$= 1.0 \text{ kHz}$$

The melanin content of the skin is responsible for the pigmentation of skin. Experimentally it has been demonstrated that the wavelength of least absorption for melanin is in the 800 nm range. Use of this wavelength is important because it is a minimum point of absorption for persons of all skin color.

The above information establishes the parameters required for the laser 10 used for breast imaging. These parameters are summarized in the table below.

| PARAMETERS | UNITS |
|---|---|
| Wavelength | 700–1100 nm, preferably 800 nm |
| Average Power | 0.5 watt |
| Energy per pulse | 100–500 µJ |
| Repetition Rate | 1 kHz–10 kHz, preferably 1 kHz–5 kHz |
| Pulse Width | less than 150 ps, preferably 50–100 ps |

One choice of the laser 10 is a mode-locked titanium-:sapphire (Ti:s) laser seeding a Ti:s regenerative amplifier laser.

Figure 23:
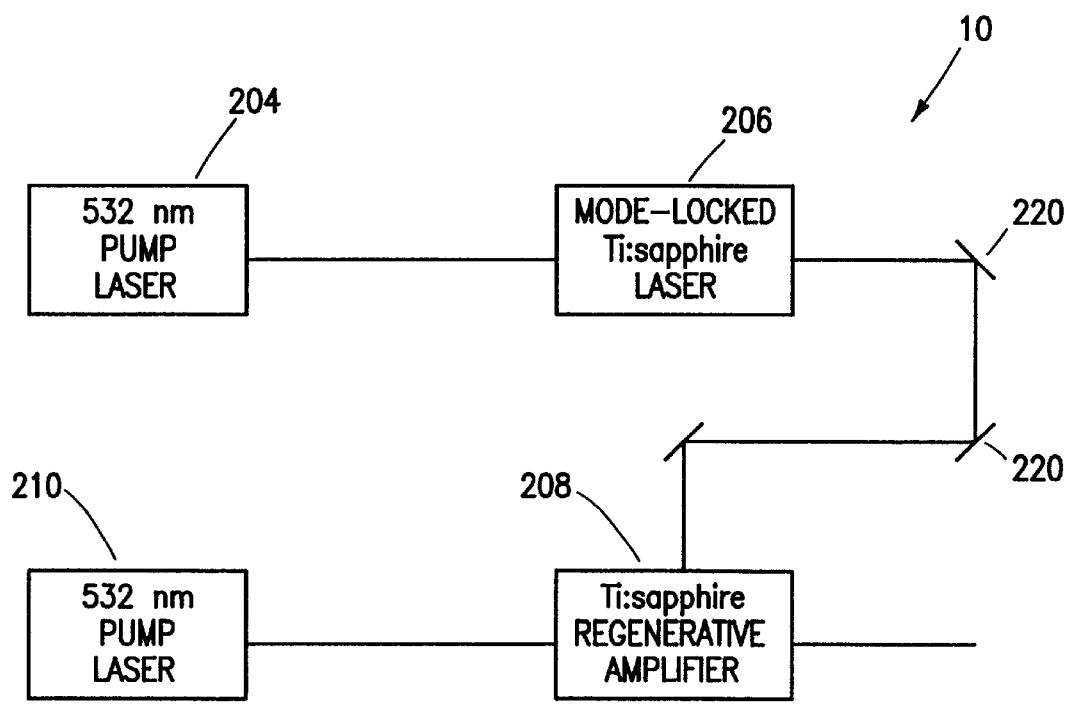
FIG. 23 is a block diagram of a laser system used in the present invention.

Referring to FIG. 23, the laser 10 used in the present invention is disclosed therein. The laser 10 includes a diode pumped solid-state laser 204 producing 532 nm light and is used to pump a mode-locked titanium:sapphire (Ti:s) laser 206. The output of the laser 206 is in the 790 to 800 nm wavelength range at a repetition rate of approximately 82 Mhz with a pulse width of about 60 picoseconds and is used as a low power input to a Ti:s regenerative amplifier 208. The regenerative amplifier 208 reduces the repetition rate and increases the energy per pulse. The regenerative amplifier 208 is powered by a flash-lamp pumped laser 210 producing 532 nm laser pulses at a 1 kHz repetition rate. Various turning mirrors 220 are used to fold the optical path to reduce the space requirement for the lasers.

The laser 204 is model Millennia, available from Spectra Physics Corp., Mountain View, Calif. The laser 206 is Model Tsunami, Spectra Physics Corp. The laser 208 is model Spitfire, Spectra Physics Corp. The laser 210 is model Magellan, Spectra Physics Corp.

Although laser 10 is disclosed as comprising of several components, a single laser meeting the required parameters is possible.

While this invention has been described as having preferred design, it is understood that it is capable of further modification, uses and/or adaptations following in general the principle of the invention and including such departures from the present disclosure as come within known or customary practice in the art to which the invention pertains, and as may be applied to the essential features set forth, and fall within the scope of the invention or the limits of the appended claims.

I claim:

1. A detector array for a laser imaging apparatus, comprising:
   a) a plurality of detectors disposed in an arc around an opening in which an object to be scanned is disposed;
   b) a multi-gain amplifier circuit connected to each detector; and
   c) said multi-gain amplifier circuit including a high-gain stage, a medium-gain stage and a low-gain stage, each connected in parallel to each other.

2. A detector array as in claim 1, wherein:
   a) said high-gain stage includes a plurality of amplifiers connected in series.

3. A detector array as in claim 1, wherein:
   a) said high-gain stage includes first, second and third amplifiers connected in series;
   b) said medium-gain stage includes a fourth amplifier connected in parallel to said third amplifier and in series with said first and second amplifiers; and
   c) a voltage divider connected between said second and fourth amplifiers.

4. A detector array as in claim 1, wherein:
   a) said high-gain stage includes a first amplifier;
   b) said low-gain stage includes a second amplifier connected in series with said first amplifier; and
   c) a voltage divider connected in series between said first and second amplifiers.

5. A detector array as in claim 1, wherein:
   a) each of said high-gain stage, medium-gain stage and low-gain stage includes a sample switch, a RC circuit and an integrator connected in series.

6. A detector array as in claim 5, wherein:
   a) said sample switch is a diode bridge circuit.

7. A detector array as in claim 1, and further comprising:
   a) a plurality of housings each including an open front end and a rear end;
   b) a plurality of fiber optic cables having first and second ends, said first ends being operably associated with respective said rear ends; and
   c) said plurality of detectors are operatively disposed at respective second ends.

8. A detector array as in claim 7, and further comprising:
   a) a first lens disposed within each of said housings intermediate of said front and rear ends; and
   b) a second lens operably associated with each of said fiber optic cable first ends.

9. A detector array as in claim 8, wherein:
   a) said first lens is a plano-convex lens.

10. A detector array as in claim 8, wherein:
    a) said second lens is a ball lens.

11. A detector array for a laser imaging apparatus, comprising:
    a) a plurality of detectors disposed in an arc around an opening in which an object to be scanned is disposed;
    b) a multi-gain amplifier circuit means connected to the output of each detector; and
    c) said multi-gain amplifier circuit means including a high-gain stage means, a medium-gain stage means and a low-gain stage means connected in parallel to each other for accommodating a wide range in output of each detector.

12. A photodetection circuit for use in a laser imaging apparatus, comprising:
    a) a photodetector having an output signal responsive to a laser pulse exiting from a breast being scanned by a laser beam;
    b) a multi-gain preamplifier circuit connected to the output signal of said photodetector;
    c) a switch connected to the output of said multi-gain preamplifier for sampling the output signal of said photodetector thereby to generate a sampled output having a width;
    d) a RC circuit for spreading the width of the sampled output signal;
    e) an amplifier connected to the output of said RC circuit;
    f) an integrator for integrating the sampled output signal;
    g) a time-gating circuit operably connected to said switch, said time-gating circuit being effective to open and close said switch at regular intervals of time during the occurrence of the photodetector output signal; and h) a laser pulse synchronization circuit operably connected to said time-gating circuit, said laser pulse synchronization circuit for providing a signal to said time-gating circuit as to when the laser pulse is expected to arrive at said photodetector.

13. A photodetection circuit as in claim 12, wherein:

a) said switch is a diode bridge circuit.

14. A photodetection circuit as in claim 12, wherein:

a) said time-gating circuit is a programmable delay chip.

15. A photodetection circuit as in claim 12, wherein:

a) said time-gating switch provides a signal to operate said switch a sufficient number of times to effectively sample the output signal of said photodetector.

16. A photodetection circuit as in claim 12, wherein:

a) said multi-gain preamplifier circuit includes first, second and third gain stages connected in parallel to each other.

17. A method for collecting data for use in image reconstruction of an object being scanned, comprising:

a) impinging a laser beam at a point on the object;

b) detecting the laser beam exiting from the object with a plurality of detectors disposed in an arc around the object being scanned;

c) amplifying the output signal of each detector through a multi-gain amplifier circuit to generate multiple outputs from each detector;

d) sampling each multiple output of the multi-gain amplifier circuit;

e) integrating each multiple output of the multi-gain amplifier circuit to provide data for image reconstruction; and f) orbiting the detectors and the laser beam to another point on a circle and repeating steps a) through e) until a complete circle has been traversed.

18. A method as in claim 17, wherein the multi-gain amplifier circuit is implemented with first, second and third gain stages connected in parallel to each other.

* * * * *